US008936934B2

(12) United States Patent
Coger et al.

(10) Patent No.: US 8,936,934 B2
(45) Date of Patent: Jan. 20, 2015

(54) BIOREACTOR ASSEMBLY AND ASSOCIATED METHODS (75) Inventors: Robin Coger, Matthews, NC (US); Mei Niu, Tampa, FL (US)

(73) Assignee: University of North Carolina at Charlotte, Charlotte, NC (US)

(*) Notice: Subject to any disclaimer, the term of this patent is extended or adjusted under 35 U.S.C. 154(b) by 441 days.

(21) Appl. No.: 12/935,351

(22) PCT Filed: Sep. 30, 2008

(86) PCT No.: PCT/US2008/078219
§ 371 (c)(1),
(2), (4) Date: Sep. 29, 2010

(87) PCT Pub. No.: WO2009/123657
PCT Pub. Date: Oct. 8, 2009

(65) Prior Publication Data
US 2011/0020863 A1    Jan. 27, 2011

Related U.S. Application Data (60) Provisional application No. 61/041,325, filed on Apr. 1, 2008.

(51) Int. Cl.
*C12M 1/22* (2006.01)
*C12M 3/00* (2006.01)
*C12M 1/00* (2006.01)

(52) U.S. Cl.
CPC .............. *C12M 23/34* (2013.01); *C12M 29/04* (2013.01); *C12M 21/08* (2013.01)
USPC .................. 435/305.2; 435/305.1; 435/304.1; 435/303.1; 435/289.1; 435/288.4

(58) Field of Classification Search
CPC ...... C12M 23/34; C12M 29/04; C12M 21/08; C12M 23/42; C12M 23/44; C12M 23/48
USPC ...................... 435/305.2, 305.1, 303.1, 289.1
See application file for complete search history.

(56) References Cited

U.S. PATENT DOCUMENTS 3,837,745 A * 9/1974 Acker et al. .................. 356/440
4,178,345 A * 12/1979 Terk .............................. 422/430

(Continued)

OTHER PUBLICATIONS

Miskon et al, "Radial Flow Type Bioreactor for Bioartificial Liver Assist System Using PTFE Non-Woven Fabric Coated with Polyamino Acid Urethane Copolymer", Macromolecular Symposia: 2007, vol. 249-250, pp. 151-158.

(Continued)

*Primary Examiner* — Nathan Bowers
(74) *Attorney, Agent, or Firm* — Clements Bernard PLLC; Christopher L. Bernard; Lawrence A. Baratta, Jr.

(57) ABSTRACT

A bioreactor assembly, including: a housing internally defining a plurality of reaction chambers; a medium flow supply line associated with each of the plurality of reaction chambers, wherein the medium flow supply line associated with each of the plurality of reaction chambers is operable for delivering a medium flow to each of the plurality of reaction chambers; and one or more framed membrane cartridges selectively disposed within each of the plurality of reaction chambers, wherein each of the one or more framed membrane cartridges disposed within each of the plurality of reaction chambers is operable for holding a biochemically active material that is reacted when exposed to the medium flow.

20 Claims, 7 Drawing Sheets

(56) References Cited

U.S. PATENT DOCUMENTS

| | | | |
|---|---|---|---|
| 4,865,813 A * | 9/1989 | Leon | 422/82.05 |
| 5,688,687 A | 11/1997 | Palssou et al. | |
| 6,506,346 B1 * | 1/2003 | Monro | 422/559 |
| 6,794,183 B2 * | 9/2004 | Wildi et al. | 435/289.1 |
| 7,303,676 B2 | 12/2007 | Husain et al. | |
| 2003/0017142 A1 * | 1/2003 | Toner et al. | 424/93.7 |
| 2003/0040104 A1 * | 2/2003 | Barbera-Guillem | 435/286.2 |
| 2004/0106184 A1 | 6/2004 | Senesac | |
| 2007/0037275 A1 | 2/2007 | Shuler et al. | |
| 2008/0194017 A1 * | 8/2008 | Esser et al. | 435/307.1 |
| 2009/0144494 A1 * | 6/2009 | Lin et al. | 711/112 |

OTHER PUBLICATIONS

Kawada et al., "Massive Culture of Human Liver Cancer Cells in a Newly Developed Radial Flow Bioreactor SYstem: Ultrafine Structure of Functionally Enhanced Hepatocarcinoma Cell Lines", In Vitro Cell. Dev. Biol.—Animal 34:109-115, Feb. 1998.

Iwahori et al;, "Radial Flow Bioreactor for the Creation of Bioartificial Liver and Kidney", Transplantation Proceedings 37, 212-214, 2005.

Gion et al., "Evaluation of a Hybrid Artificial Liver Using a Polyurethane Foal Packed-Bed Culture System in Dogs", Journal of Surgical Research 82, 131-136, 1999.

Morsiani et al., "Long-Term Expression of Highly Differentiated Functions by Isolated Porcine Hepatocytes Perfused in a Radial-Flow Bioreactor", Artificial Organs 25(9), 740-748, 2001.

Naruse et al., Efficacy of Nonwoven Fabric Bioreactor Immobilized with Porcine Hepatocytes for Ex Vivo Xenogeneic Perfusion Treatment for Liver Failure in Dogs, Artificial Organs 25(4), 273-280, 2001.

\* cited by examiner

BIOREACTOR ASSEMBLY AND ASSOCIATED METHODS

CROSS-REFERENCE TO RELATED APPLICATION(S)

The present non-provisional patent application claims the benefit of priority of U.S. Provisional Patent Application No. 61/041,325 (Robin Coger and Mei Niu), filed on Apr. 1, 2008, and entitled "RADIAL FLOW BIOREACTOR," the contents of which are incorporated in full by reference herein.

STATEMENT REGARDING FEDERALLY SPONSORED RESEARCH OR DEVELOPMENT

The present invention was developed through private support from the Whitaker Foundation, Grant No. TF-05-0001, and in part through government support from the National Institutes of Health (NIH), Grant No. R01 DK058503-01A1. Therefore, the government has certain rights in the present invention.

FIELD OF THE INVENTION

The present invention relates generally to a bioreactor assembly and associated methods. More specifically, the present invention relates to a bioreactor assembly that utilizes and incorporates a medium flow, a plurality of customizable concentrically arranged framed membrane cartridges for cellular attachment and the like, and a modular design that allows for selected framed membrane cartridges to be removed, studied, cryo-preserved, and/or replaced in process, without otherwise disrupting the reactions taking place in the bioreactor assembly.

BACKGROUND OF THE INVENTION

In general, a bioreactor is a vessel in which a chemical reaction or process is carried out that involves an organism or biochemically active substance derived from an organism. In other words, bioreactors differ from conventional chemical reactors in that they support and control biological entities. Therefore, bioreactors must be designed to provide a higher degree of control over upsets and contaminations than conventional chemical reactors, they must provide a higher degree of selectivity, they must accommodate a wider range of reaction rates, etc. Furthermore, the evaluation of the integrity of the cell population contained within the bioreactor throughout the course of the bioreactor's use is required. While this often done by analyzing samples of the bioreactor's flow, there are benefits to being able to analyze the cell population of the bioreactor over time. The reaction parameters that must be controlled and optimized include substrate selection, amount, and configuration; cellular selection, patterning, culturing, and protection; water availability; oxygen availability; nutrient availability; temperature; pH; gas evolution; product and byproduct removal; flow rate, etc. Advantageously, bioreactors are used in the following exemplary applications, among others: bioartificial organs, organ and tissue simulation, drug discovery and testing, cell/tissue manufacturing, antibody production, and, in general, the study and use of biochemical reactions (including those involving organisms, substances derived from or affecting organisms, cellular structures, etc.). It will be readily apparent to those of ordinary skill in the art that there are other applications not specifically included in this list, both existing and future.

Tissue loss and organ failure are unfortunately suffered by patients on a daily basis. Yet for acute clinical cases, transplantation is the only end stage treatment currently available. In reality, the supply of donated tissues and organs is very limited, and interim options are needed. The use of bioreactors that provide an environment for maintaining cells while enabling them to perform key functions offers hope as an interim treatment. In such applications, these bioreactors are essentially bridges to transplantation. In the future, they may serve as substitutes for transplantation as well.

In the case of bio-artificial liver (BAL) devices, for example, a bioreactor is used to support viable hepatocytes, such that these hepatocytes may express high levels of differentiated function. BAL devices are typically classified as one of several types: capillary hollow fiber devices, suspension and encapsulation chambers, and perfused beds and scaffolds. Capillary hollow fiber devices have been rapidly developed for clinical trials. Unfortunately, these devices have the inherent physical limitations of constrained total mass diffusion distances, reduced capacities for cellular mass maintenance, and non-uniform cellular distributions. Suspension and encapsulation chambers provide a uniform microenvironment and the potential for scale up, but they offer poor cellular stability (e.g. suspension chambers) and barriers to nutrient transport (e.g. encapsulation chambers). In both cases, cells are exposed to unacceptably high shear forces. Perfused beds and scaffolds solve some of these problems, but, unfortunately, experience non-uniform perfusion, the clogging of membrane pores, and may also expose cells to unacceptably high shear forces. All of these devices make it difficult, if not impossible, to remove a fraction of the cellular space in process, without otherwise disrupting the reactions taking place.

Thus, what is still needed in the field is a bioreactor design that solves some or all of these problems.

In general, tissue function is modulated by the communication of cells with extracellular matrices, soluble factors, and other cells. The technologies used to explore the latter interaction (e.g., cell-to-cell)—such as micro-fabrication, micro-patterning, and the like—have typically been applied to flat plate in vitro cultures. Because flat plate in vitro cultures offer low surface area-to-volume ratios, it is difficult to scale them up to the cellular masses associated with bioreactors. Microfabrication and micro-patterning techniques, such a photolithography, photo-patterning, micro-contact printing, inkjet printing, laser guided direct writing, and cell spraying have been used to develop heterogeneous two-dimensional and three-dimensional co-cultures. Although co-culturing hepatocytes, the liver parenchymal cell, with support cells positively impacts hepatocyte function, for example, micro-fabrication and micro-patterning techniques may not readily be implemented in any of the BAL devices described above.

Thus, what is still needed in the field is a bioreactor design that provides an adaptable cellular space, among other things.

BRIEF SUMMARY OF THE INVENTION

In various exemplary embodiments, the present invention provides a bioreactor assembly that utilizes and incorporates a quadrant-specific medium (e.g., blood, plasma, blood equivalent (e.g., nutrient media), or other fluid designed to interact with the biological entities of the bioreactor) flow; a plurality of customizable concentrically arranged framed membrane cartridges for the packing of cells, tissues, and the like; and a modular design that allows for selected framed membrane cartridges to be removed, studied, cryo-preserved, and/or replaced in process, while only minimally disrupting the reactions taking place in the bioreactor assembly. In other words, the bioreactor assembly of the present invention incorporates a novel cellular support structure that is modular in nature. It is capable of accommodating functional sized tissues (e.g. consisting of about than $2\times10^8$ cells of 30-micron diameter in its initial embodiment) and a wide range of attachment dependent cells. Advantageously, the bioreactor assembly of the present invention is fully scalable and may be stored, for off-the-shelf availability.

In one exemplary embodiment, the present invention provides a bioreactor assembly, including: a housing internally defining a plurality of reaction chambers; a medium flow supply line associated with each of the plurality of reaction chambers, wherein the medium flow supply line associated with each of the plurality of reaction chambers is operable for delivering a medium flow to each of the plurality of reaction chambers; and one or more framed membrane cartridges selectively disposed within each of the plurality of reaction chambers, wherein each of the one or more framed membrane cartridges disposed within each of the plurality of reaction chambers is operable for holding a biochemically active material that is reacted when exposed to the medium flow. The housing includes a perimeter wall, a bottom wall, and one or more internal walls that collectively define the plurality of reaction chambers. Preferably, the one or more internal walls prevent fluid communication among the plurality of reaction chambers. Preferably, the medium flow delivered to each of the plurality of reaction chambers is a medium flow. The one or more framed membrane cartridges disposed within each of the plurality of reaction chambers are disposed substantially concentrically about a central axis of the housing. The one or more framed membrane cartridges disposed within each of the plurality of reaction chambers are disposed in a substantially vertical orientation. Each of the one or more framed membrane cartridges includes one or more frame members and one or more membrane substrates selectively disposed within and retained by the one or more frame members. The biochemically active material is selectively disposed one of on and between the one or more membrane substrates. Optionally, one or more of the one or more membrane substrates are substantially porous, such that fluid transport may take place there through. The bioreactor assembly also includes a rack that engages the housing and to which the one or more framed membrane cartridges are attached. The bioreactor assembly further includes a cover operable for selectively engaging and environmentally sealing the housing.

In another exemplary embodiment, the present invention provides a bioreactor method, including: providing a housing internally defining a plurality of reaction chambers; associating a medium flow supply line with each of the plurality of reaction chambers, wherein the medium flow supply line associated with each of the plurality of reaction chambers is operable for delivering a medium flow to each of the plurality of reaction chambers; and selectively disposing one or more framed membrane cartridges within each of the plurality of reaction chambers, wherein each of the one or more framed membrane cartridges disposed within each of the plurality of reaction chambers is operable for holding a biochemically active material that is reacted when exposed to the medium flow. The housing includes a perimeter wall, a bottom wall, and one or more internal walls that collectively define the plurality of reaction chambers. Preferably, the one or more internal walls prevent fluid communication among the plurality of reaction chambers. Preferably, the medium flow delivered to each of the plurality of reaction chambers is a medium flow. The one or more framed membrane cartridges disposed within each of the plurality of reaction chambers are disposed substantially concentrically about a central axis of the housing. The one or more framed membrane cartridges disposed within each of the plurality of reaction chambers are disposed in a substantially vertical orientation. Each of the one or more framed membrane cartridges includes one or more frame members and one or more membrane substrates selectively disposed within and retained by the one or more frame members. The biochemically active material is selectively disposed one of on and between the one or more membrane substrates. Optionally, one or more of the one or more membrane substrates are substantially porous, such that fluid transport may take place there through. The bioreactor method also includes providing a rack that engages the housing and to which the one or more framed membrane cartridges are attached. The bioreactor method further includes providing a cover operable for selectively engaging and environmentally sealing the housing.

In a further exemplary embodiment, the present invention provides a bioreactor assembly, including: a housing internally defining a plurality of reaction chambers; a medium flow supply line associated with each of the plurality of reaction chambers, wherein the medium flow supply line associated with each of the plurality of reaction chambers is operable for delivering a medium flow to each of the plurality of reaction chambers; and one or more framed membrane cartridges selectively disposed within each of the plurality of reaction chambers, wherein each of the one or more framed membrane cartridges disposed within each of the plurality of reaction chambers is operable for holding a biochemically active material that is reacted when exposed to the medium flow, and wherein one or more of the one or more framed membrane cartridges disposed within a given reaction chamber may be selectively removed without disrupting reactions taking place in other reaction chambers. Preferably, the bioreactor assembly is maintained at predetermined environmental conditions. The bioreactor assembly is used in an application selected from the group consisting of a bioartificial organ application, an organ modeling application, an organ simulation application, a drug discovery application, a drug testing application, a cell/tissue manufacturing application, an antibody production application, and another biochemical reaction application.

It should be noted that, although the bioreactor assembly of the present invention is described herein largely in terms of liver support applications, its broader applicability is not so limited, as those of ordinary skill in the art will readily understand and appreciate. Many applications that are currently known and that have yet to be developed are contemplated by the present invention. At present, bioreactors are used in artificial organ, organ simulation, drug discovery and testing, and, in general, biochemical reaction (including those involving organisms, substances derived from organisms, cellular structures, etc.) applications, as examples. Quite simply, the bioreactor assembly of the present invention may be used in any application that a bioreactor of any type is suitable for.

BRIEF DESCRIPTION OF THE DRAWINGS

The present invention is illustrated and described herein with reference to the various drawings, in which like reference numbers are used to denote like assembly components/method steps, as appropriate, and in which.

DETAILED DESCRIPTION OF THE INVENTION

Again, the present invention provides a bioreactor assembly that utilizes and incorporates a medium flow, a plurality of customizable concentrically arranged framed membrane cartridges for cellular attachment and the like, and a modular design that allows for selected framed membrane cartridges to be removed, studied, cryo-preserved, and/or replaced in process, without otherwise disrupting the reactions taking place in the bioreactor assembly. In other words, the bioreactor assembly of the present invention incorporates a novel cellular support structure that is modular in nature. It is capable of accommodating functional sized tissues (e.g. consisting of more than $2 \times 10^8$ cells of 30-micron diameter) and a wide range of attachment dependent cells. Advantageously, the bioreactor assembly of the present invention is fully scalable and may be stored, for off-the-shelf availability.

Figure 1:
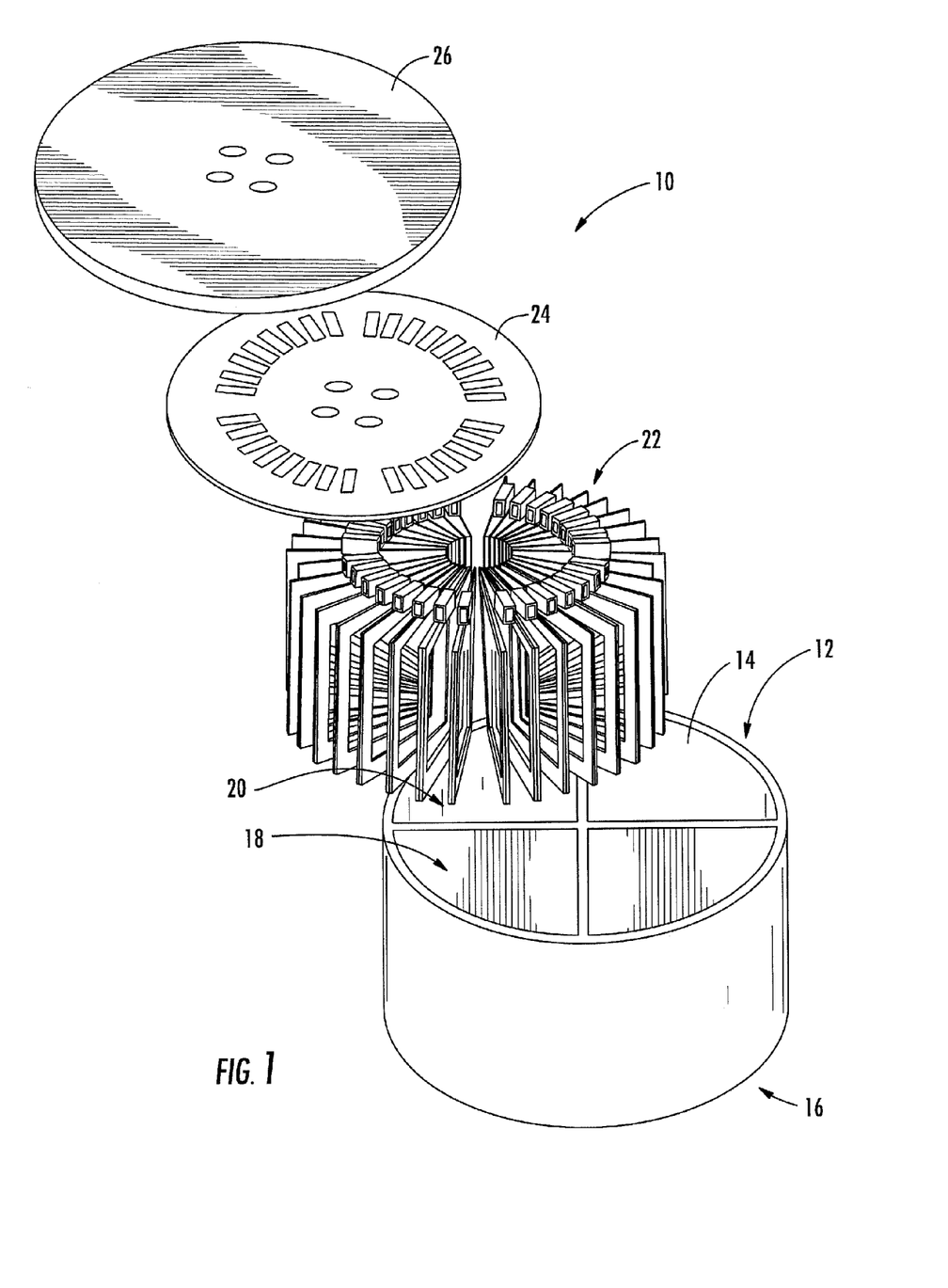
FIG. 1 is a fully exploded perspective view of one exemplary embodiment of the bioreactor assembly of the present invention, highlighting the housing, framed membrane cartridges, rack, and cover of the bioreactor assembly.

Referring to FIG. 1, in one exemplary embodiment, the bioreactor assembly 10 of the present invention includes a housing 12 defined by a circumferential wall 14 and a bottom wall 16. The interior of the housing 12 is divided into multiple reaction chambers 18 by multiple walls 20. In general, these walls 20 separate these reaction chambers 18, such that the biochemical reactions taking place in the reaction chambers 18 are isolated from one another. Optionally, in some applications, some or all of the walls 20 could include holes (not illustrated) or the like, such that the reaction chambers 18 would be in fluid communication and the biochemical reactions taking place in given reaction chambers 18 would not be isolated from one another. Preferably, the bioreactor assembly 10 has an overall height of between about 2 inches and about 5 inches, and an overall diameter or width of between about 3 inches and about 6 inches. It will be readily apparent to those of ordinary skill in the field, however, that other suitable dimensions could be utilized, as the bioreactor assembly 10 is fully scalable. Although the housing 12 of the bioreactor assembly 10 is illustrated as a substantially circular structure, it will also be readily apparent to those of ordinary skill in the field that other suitable shapes could be utilized. The housing 12 and other components of the bioreactor assembly 10 may be formed from any material that is compatible with the biochemical reactions taking place within. Exemplary materials include plastic materials and metallic materials, such as polycarbonate (PC) and stainless steel (SS). Preferably, all materials used are autoclavable.

The bioreactor assembly 10 also includes multiple customizable concentrically arranged framed membrane cartridges 22 for cellular attachment and the like, as described in greater detail below. In a preferred embodiment, each reaction chamber 18 includes multiple framed membrane cartridges 22. Advantageously, one or more framed membrane cartridges 22 may be removed from one reaction chamber 18 without disrupting the biochemical reactions taking place in other reaction chambers 18. In this sense, the bioreactor assembly 10 is modular.

The framed membrane cartridges 22 are selectively attached to a rack 24, as also described in greater detail below. This rack 24 is selectively disposed within or adjacent to the top portion of the housing 12, such that the framed membrane cartridges 22 hang in the housing 12. It will be readily apparent to those of ordinary skill in the field that other means for securing the framed membrane cartridges 22 in the housing 12 could be utilized. For example, the housing 12 could include multiples "slots" within which the framed membrane cartridges 22 are disposed.

The bioreactor assembly 10 further includes a cover 26 that is used to selectively seal the housing 12. Again, although the cover 26 of the bioreactor assembly 10 is illustrated as a substantially circular structure, it will be readily apparent to those of ordinary skill in the field that other suitable shapes could be utilized.

Figure 2:
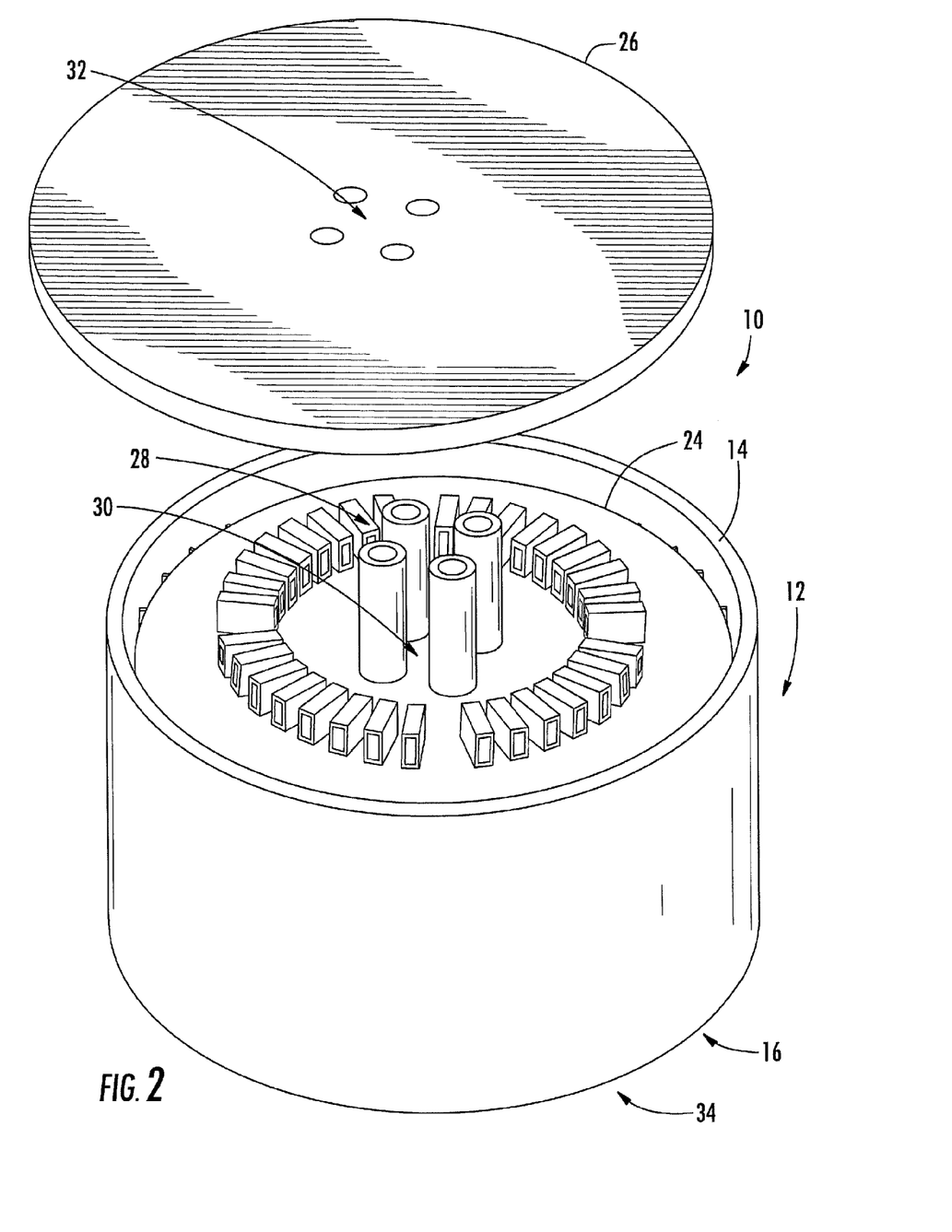
FIG. 2 is a partially exploded perspective view of the bioreactor assembly of FIG. 1, highlighting the media transport tubes of the bioreactor assembly.

Referring to FIG. 2, the bioreactor assembly 10 still further includes one or more media transport tubes 28 that selectively pass through one or more holes 30 manufactured into the rack 24, as well as one or more holes 32 manufactured into the cover 26, as well as one or more holes 34 manufactured into the bottom wall 16 of the housing 12. These media transport tubes 28 are operable for carrying one or more reaction media to and away from each of the reaction chambers 18 (FIG. 1), through an inlet at the bottom of each reaction chamber 18 and an outlet at the top of each reaction chamber 18, as illustrated. Advantageously, the one or more reaction media carried to and away from each of the reaction chambers 18 may be the same reaction media, such that the biochemical reactions taking place in each of the reaction chambers 18 is doing so under similar environmental conditions. The one or more reaction media carried to and away from each of the reaction chambers 18 may also be different reaction media, such that the biochemical reactions taking place in each of the reaction chambers 18 is doing so under different environmental conditions. In order to deliver the reaction media to each of the reaction chambers 18, the media transport tubes are equipped with appropriate fluid delivery holes or other fluid delivery mechanisms (not illustrated) within each of the reaction chambers 18. Advantageously, the bioreactor assembly 10 may be operated at full or fractional capacity due to its modular reaction chamber/media transport tube configuration.

Figure 3:
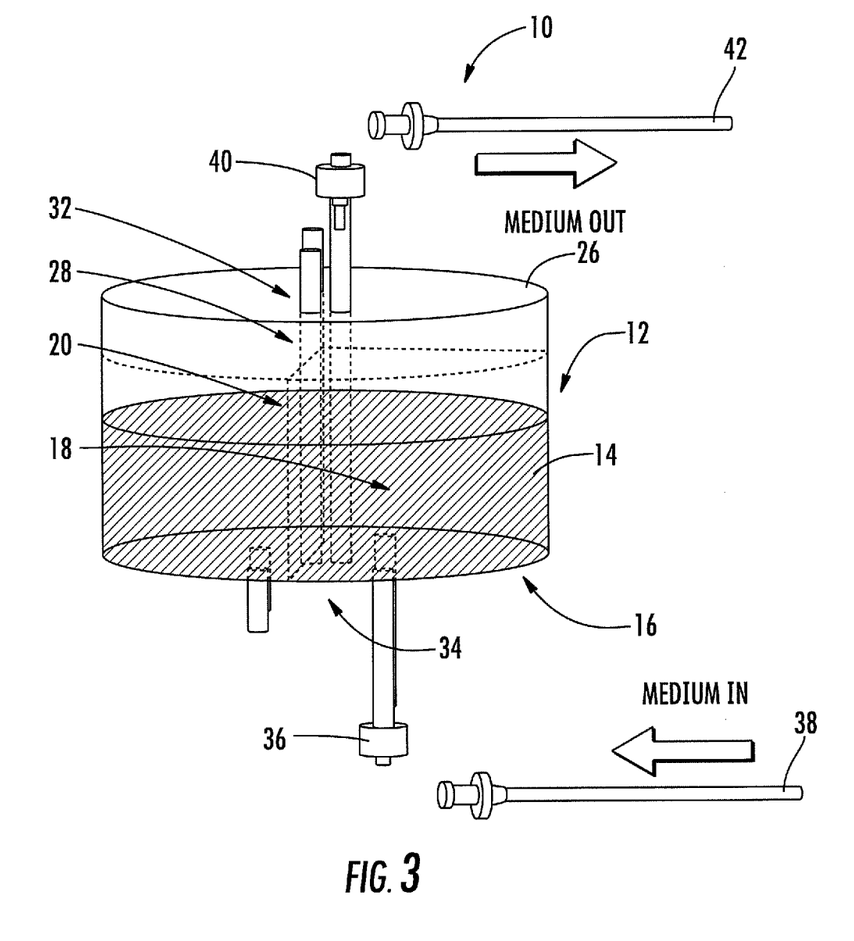
FIG. 3 is a partially transparent perspective view of the bioreactor assembly of FIGS. 1 and 2, highlighting the media transport tube connections of the bioreactor assembly.

Referring to FIG. 3, for the ease of connection, the one or more media transport tubes 28 include an inlet port 36 that is selectively connected to a media inlet line 38 and an outlet port 40 that is selectively connected to a media outlet line 42. Thus, a media flow path is established through the bioreactor assembly 10.

It should be noted that the various media illustrated and described herein are typically oxygenated nutrient media, such as blood or plasma equivalents in organ simulation and replacement applications. These media could also include any required to maintain the biochemical reaction(s) of interest.

Figure 4:
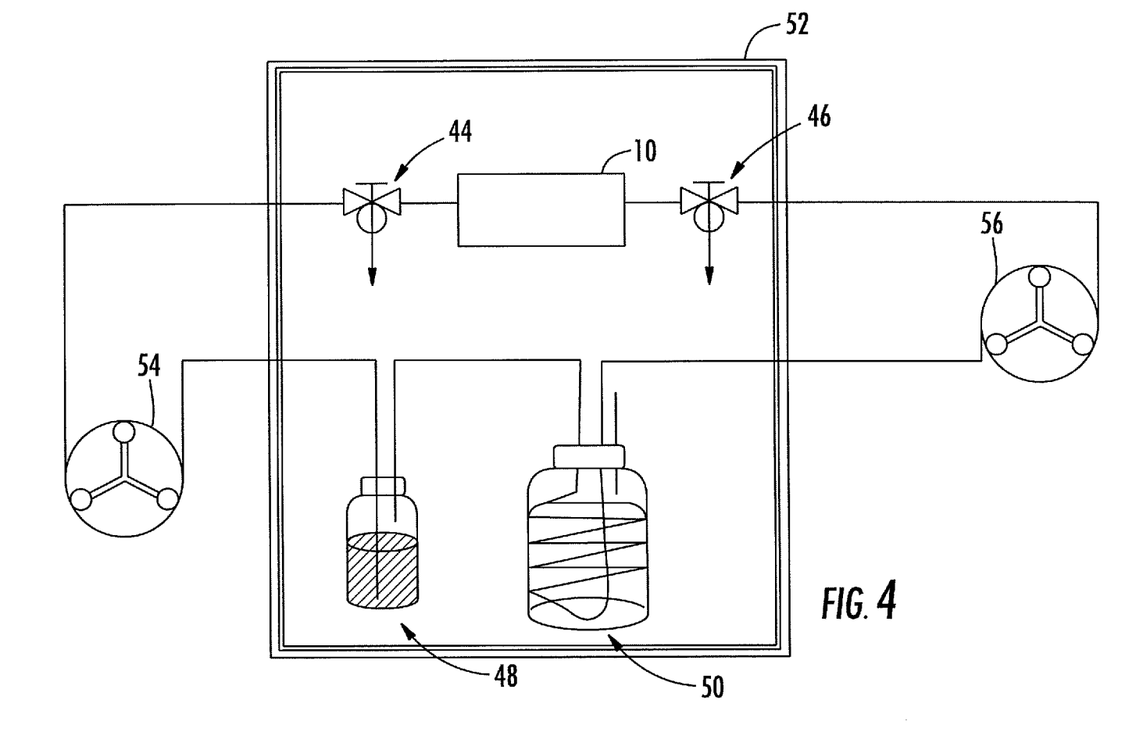
FIG. 4 is a schematic view of an overall environmental system in which the bioreactor assembly of FIGS. 1-3 is implemented.

Referring to FIG. 4, in one exemplary embodiment, the bioreactor assembly 10 is connected between a first sample point 44 and a second sample point 46, each of the sample points 44 and 46 including a valve or the like operable for providing access to the one or more reaction media entering and/or exiting the bioreactor assembly 10. Oxygen levels and the like may be monitored at these sample points 44 and 46. The bioreactor assembly 10 is connected to a media reservoir 48 and a media gas exchanger 50, operable for selectively adding gas to or removing gas from the one or more reaction media. The bioreactor assembly, 10, the sample points 44 and 46, the media reservoir 48, and the media gas exchanger 50 are disposed within an incubator 52 operable for maintain the gas, pressure, and temperature environment of the bioreactor assembly 10, such that the biochemical reactions taking place therein are maintained. In order to move the one or more transport media, the bioreactor assembly 10 is also connected between a first peristaltic pump 54 and a second peristaltic pump 56. It will be readily apparent to those of ordinary skill in the field that other overall environmental systems could be utilized.

Referring to FIG. 5, again, the bioreactor assembly 10 (FIGS. 1-4) includes multiple customizable concentrically arranged framed membrane cartridges 22 for cellular attachment and the like. In a preferred embodiment, each reaction chamber 18 (FIGS. 1 and 3) includes multiple framed membrane cartridges 22. Advantageously, one or more framed membrane cartridges 22 may be removed from one reaction chamber 18 without disrupting the biochemical reactions taking place in other reaction chambers 18. In this sense, the bioreactor assembly 10 is modular.

The framed membrane cartridges 22 are selectively attached to the rack 24. The rack 24 is selectively disposed within or adjacent to the top portion of the housing 12 (FIGS. 1-3), such that the framed membrane cartridges 22 hang in the housing 12. It will be readily apparent to those of ordinary skill in the field that other means for securing the framed membrane cartridges 22 in the housing 12 could be utilized. For example, the housing 12 could include multiples "slots" within which the framed membrane cartridges 22 are disposed.

Figure 5:
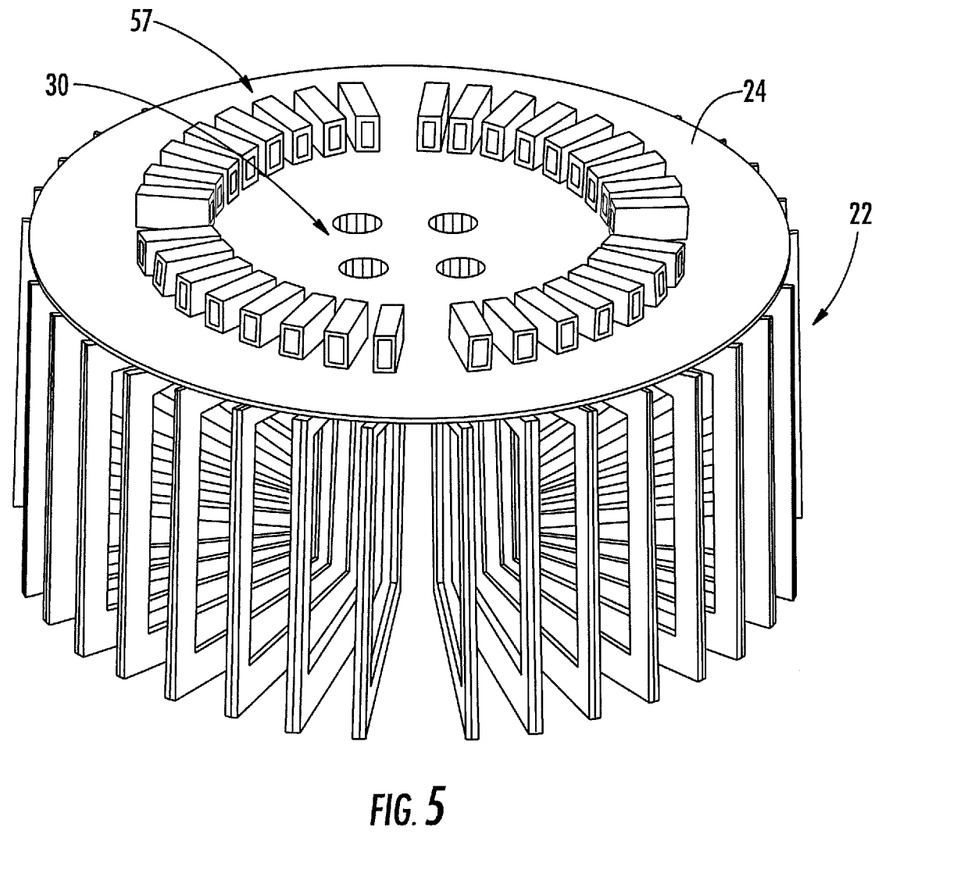
FIG. 5 is a perspective view of the framed membrane cartridges and rack of FIGS. 1 and 2 in an assembled configuration.
Figure 6:
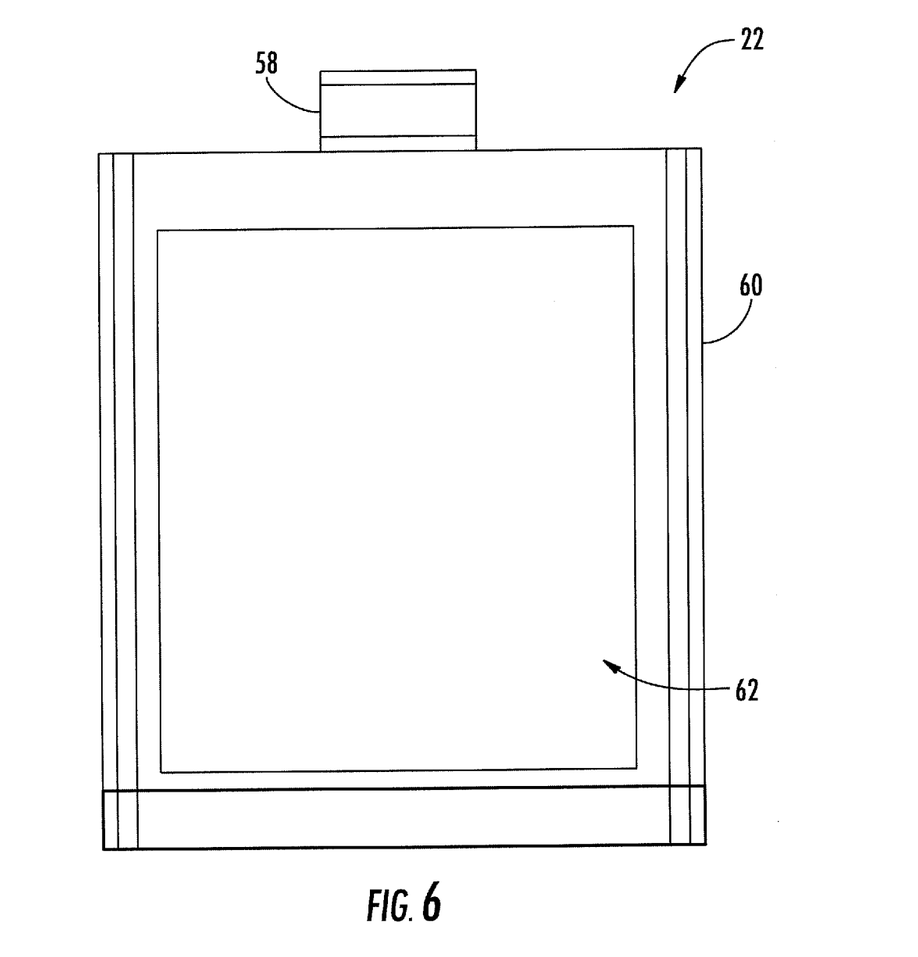
FIG. 6 is a planar view of one of the framed membrane cartridges of FIGS. 1 and 5, highlighting the frame, one or more membranes, and tab structure of the framed membrane cartridge.

Referring to FIG. 6, in one exemplary embodiment, each of the framed membrane cartridges 22 includes a frame 60 within which one or more membranes 62 are selectively disposed. Optionally, the frame 60 is a two piece frame, the two pieces interlocking such that the one or more membranes 62 are entrapped within the frame 60. A clip or the like may be used to selectively hold the two pieces together. These membranes 62 act as a substrate for cellular attachment and the like, as described in greater detail below. Preferably, the spacing between adjacent membranes 62 is on the order of a millimeter, although any suitable pacing may be used. The frame 60 includes a tab structure 58 that is configured to engage a corresponding slot 57 (FIG. 5) that is manufactured into the rack 24 (FIG. 5). Again, it will be readily apparent to those of ordinary skill in the field that other means for securing the framed membrane cartridges 22 to the rack 24 could be utilized.

Figure 7:
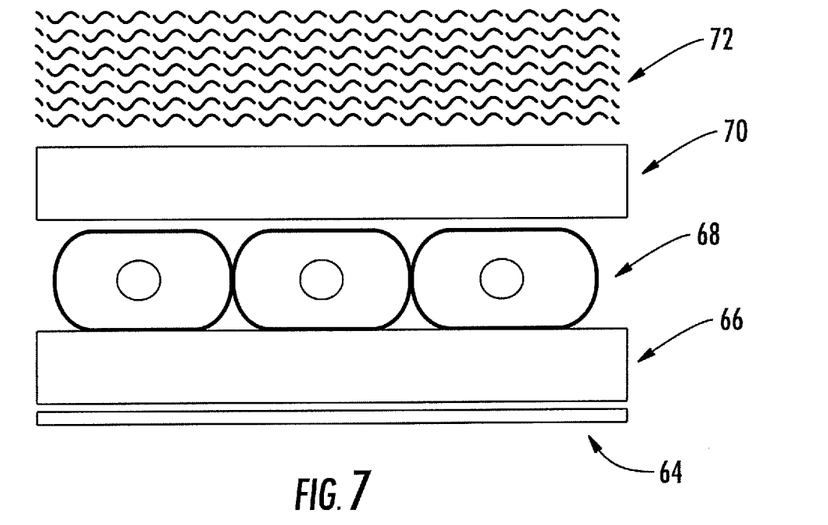
FIG. 7 is a schematic view of one exemplary embodiment of a membrane configuration that may be utilized with the one or more membranes of FIG. 6.

Referring to FIG. 7, in one exemplary embodiment, a membrane configuration that may be utilized with the one or more membranes 62 (FIG. 6) includes a substrate 64, such as a plastic substrate or the like. A first layer 66, such as a collagen layer or the like, is deposited on the substrate 64 via coating dried type I collagen film or the like. This first layer 66 serves as the attachment layer for a cellular layer 68 or other biochemically active material that carries out the biochemical reactions of interest. A second layer 70, such as another collagen layer or the like, is deposited on the cellular layer 68 or other biochemically active material via placing type I collagen gel with a thickness of about 500 microns to create a modified sandwich culture configuration or the like. This second layer 70 serves as a protective layer for the cellular layer 68 or other biochemically active material, protecting it from shear forces caused by the adjacent medium flow 72 while allowing nutrient transport there through.

Figure 8:
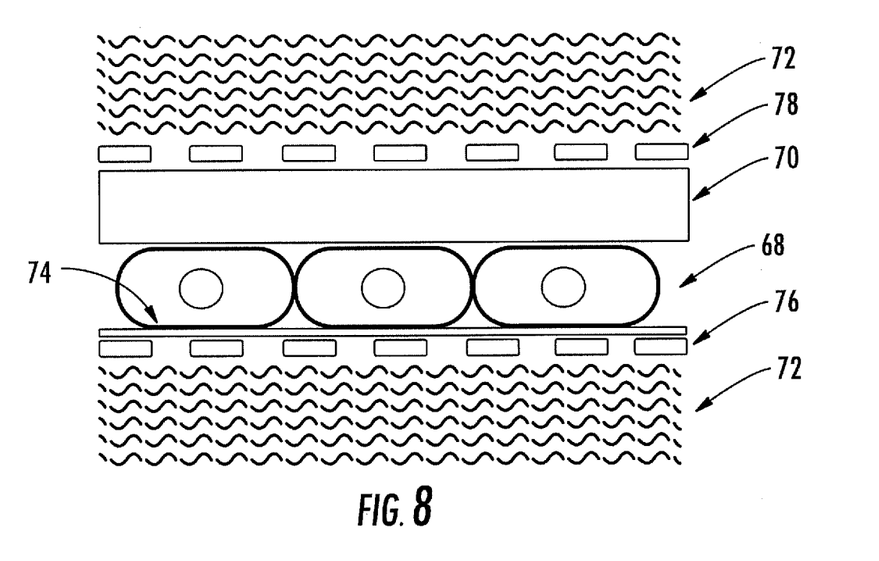
FIG. 8 is a schematic view of another exemplary embodiment of a membrane configuration that may be utilized with the one or more membranes of FIG. 6.

Referring to FIG. 8, in another exemplary embodiment, a membrane configuration that may be utilized with the one or more membranes 62 (FIG. 6) includes a first layer 74, such as a dried collagen layer or the like. Again, this first layer 74 serves as the attachment layer for the cellular layer 68 or other biochemically active material that carries out the biochemical reactions of interest. The second layer 70, such as the other collagen layer or the like, is deposited on the cellular layer 68 or other biochemically active material via placing type I collagen gel with a thickness of about 500 microns or the like. In this exemplary embodiment, the first layer 74, the cellular layer 68 or other biochemically active material, and the second layer 70 are "sandwiched" between a first porous membrane 76 and a second porous membrane 78. These porous membranes 76 and 78 serve as protective layers for the cellular layer 68 or other biochemically active material, protecting it from shear forces caused by the adjacent media flows 72 while allowing nutrient transport there through. The porous membranes 76 and 78 may be, for example, permeable polytetrafluoroethylene (PTFE) membranes of 30 μm thickness and 0.4 μm pore size. Other suitable membranes may be made of cellulose or modified cellulose membrane, collagen patch, polysulfone, or other appropriate tissue scaffold, for example.

Although two exemplary membrane configurations have been illustrated and described, it will be readily apparent to those of ordinary skill in field that other configurations could be used, both in terms of layer material selection and ordering. In general, membrane materials are selected for their various properties—including pore size, hydrophilicity, hydrophobicity, etc.

Experimental Setup

PC cartridge frames were machined using a computer numerical control machine. SS cartridge frames were machined using a laser cutter. To prepare the PC cartridge frames for use, they were cleaned using sandpaper and by immersing them in 95% ethanol, then sterilized by autoclaving at 121° C./15 psig using a 30-minute cycle in preparation for tissue culture use. To prepare the SS cartridge frames for use, an initial cleaning was performed to remove all oxide particles and heat tint, followed by a 30-minute soak in a 20% nitric acid bath at 60° C. (i.e. a passivation). To remove the residual acid, the SS cartridge frames were then thoroughly rinsed in de-ionized water. Finally, the SS cartridge frames were sterilized by autoclaving at 121° C./15 psig using a 30-minute cycle in preparation for tissue culture use. Prior to reusing either the PC or SS cartridge frames, fine sandpaper was used to clean their surfaces; followed by autoclaving at 121° C./15 psig using a 30-minute cycle.

Prior to using the PTFE membranes, the membranes were first autoclaved using a 15-minute liquid cycle at 121° C. Next, the membranes were attached to each cartridge frame using a cyanoacrylate adhesive. The assembled cartridge frame-membrane assemblies were then stored within a biosafety cabinet for at least 24 hours to allow the cyanoacrylate adhesive to fully cure.

Before using the cartridge frame-membrane assemblies for tissue culture, they were further sterilized by immersion in 95% ethanol until membranes appeared to be transparent. The cartridge frame-membrane assemblies were then sterilized via immersion in 70% ethanol for a minimum of 1 hour. The cartridge frame-membrane assemblies were then washed three times in saline solution (i.e. 0.9% NaCl), with a 20-minute soak included in the second wash. The cartridge frame-membrane assemblies were then dried in preparation for making the tissue equivalents they would support.

In order to prepare the bioreactor assembly for use, other critical parts (e.g. the reaction chambers, all connectors, all silicone stoppers, various tubing, as well as parts of the dynamic system) were sterilized prior to use by rinsing them first with 90% ethanol, then with 70% ethanol, then twice with 1× phosphate buffered saline (PBS).

The circulation system used included a medium reservoir for removing gas bubbles from the medium; a gas exchanger made of gas permeable silastic tubing with a length of 5 m, ED×OD=1.47×1.96 mm; a multi-function meter for documenting the level of dissolved $O_2$ within the medium and the pH of the nutrient medium; a peristaltic pump coupled to a flow meter for directing the flow of the liquid nutrients; and an incubator for maintaining the bioreactor assembly at 37° C. with 5% $CC_2$/95% air. The priming volume of the circuit was 320 ml. The tissue culture medium was perfused at a rate of 55-60 ml/min starting on day three post-isolation and was changed on day six and day twelve. The flow rate was checked regularly.

For each reaction chamber of the bioreactor assembly, the cellular spaces (i.e. the cartridge frame-membrane assemblies) were attached to the rack and suspended vertically. This unique bioreactor design allows for the easy removal of a single (or multiple) cartridge frame-membrane assemblies from the overall system. The design of the cartridge frame/membrane assemblies makes the bioreactor assembly adaptable for use in supporting a wide range of tissue equivalents. As described above and below, the current investigation demonstrated its applicability to a cellular space consisting of hepatocytes sandwiched between two layers of type I collagen, for example. To ensure stabilization of the cells within the cartridge for 24 hours prior to securing them within the bioreactor assembly, the cultures were first incubated for 24 hours within a 100 mm tissue culture dish at 37° C. and 5% $CO_2$/95% air; then relocated under sterile conditions to the rack of the bioreactor assembly.

Specifically, rat hepatocytes were isolated from male Sprague Dawley rats weighing 180-220 g by collagenase perfusion using a method modified from Seglen (1976). The liver was perfused with collagenase solution (140 mg/ml) through the portal vein, and the digested liver was then filtered through a nylon mesh with a pore size of 105 µm. The hepatocytes were then separated from the non-parenchymal cell fractions by centrifugation at 50 g for 3 minutes. The viability of the hepatocytes, evaluated via trypan blue exclusion, was 88-95%. When the cellular viability was below 85%, percoll centrifugation was performed. The hepatocytes were then re-suspended in culture medium containing Dulbecco's Modified Eagle Medium (DMEM) supplemented with 3.7 g of sodium bicarbonate, insulin (500 U/L), glucagon (7 µg/L), epidermal growth factor (20 µg/L), hydrocortisone (7.5 mg/L), penicillin G (10,000 U/ml), streptomycin (10 mg/ml), amphotericin B (25 mg/ml), and 10% fetal bovine serum.

Static sandwich cultures in (35 mm diameter) tissue culture plates were used as the controls throughout the experiments. The collagen type I gel was first prepared by adding eight parts of 1.1 mg/ml PureCol collagen to one part of 10×DMEM. The pH of the solution was adjusted to 7.4 by adding 0.1 N NaOH or 0.01 N HCl. In the tissue culture plates, 0.5 ml of collagen was coated and incubated for at least one hour at 37° C., 5% C>2/95% air to allow gelation. Then 1 ml of $2.0 \times 10^6$ cells/ml hepatocytes were seeded in each tissue culture plate to achieve a seeding density of $2.1 \times 10^5$ cells/cm$^2$. The medium was then changed after 1 hour to remove unattached cells from the culture. After 24 hours, 0.5 ml of collagen gel was added to each tissue culture plate and allowed to gel for 45 minutes at 37° C. in a 5% $CO_2$/95% air incubator. Following this, the culture medium was replaced daily.

A modified sandwich culture was also used for the cellular space. As compared to the previous static sandwich culture, the membrane of the bottom unit of the cartridge was first coated with a dried collagen film. The collagen film was prepared by diluting the stock Purcol collagen (3.1 mg/ml) 1:4 in 70% ethanol (one part collagen and three parts 70% ethanol) and vortexing to mix. Then, 1 ml of the diluted collagen was evenly coated on the membrane of the bottom unit. After incubating the collagen coated membrane overnight at 37° C., 5% $CO_2$, 2 ml of hepatocytes (density: $2.0 \times 10^6$ cells/ml) were seeded. The final seeding density of hepatocytes for each cartridge was $2.1 \times 10^5$ cells/cm$^2$. The medium was changed after 1 hour incubation to remove excess unattached hepatocytes. After 24 hours of culture, 1 ml of collagen gel was added on top of the layer of cells and allowed to gel at 37° C. in a 5% $CO_2$/95% air incubator for 45 minutes. It should be noted that, to this point, the membrane of the bottom unit was always exposed to air on its bottom side through the use of supports under the cartridge frames. After fixing the top unit of the cartridge onto the bottom unit (clips were used to close the bottom and top units of the cartridge properly), the cartridge placed in a tissue culture plate, 100 mm in diameter, and 15 ml of medium was added for culture.

The effectiveness of an individual cartridge in supporting cells was first evaluated using hepatocytes cultured within both static and dynamic systems. In the static culture system, a single cartridge containing hepatocytes was sandwiched between collagen type I gel and placed in a tissue culture plate (100 mm in diameter) and incubated at 37° C., 5% $CO_2$/95% air. To maintain the cell culture, 15 ml of cell culture medium was replaced every other day from day 2 on. In the dynamic culture system, two cartridges, which were identical to the hepatocyte supporting cartridges of the static system, were placed in a modified tissue culture plate (100 mm in diameter), retrofitted with an inlet and an outlet to ensure medium flow. This dynamic system was also incubated at 37° C., 5% $CO_2$/95% air. 50 ml of culture medium was circulated in the flow circuit, with a flow rate of 30 ml/min, and replaced every other day. Two cartridges were used for the dynamic system to increase the cell number to avoid excessive dilution of the cells' metabolites within the medium. For both the static and dynamic culture systems, 1 ml of supernatant was sampled for cell function analysis from day 3 of the culture.

To test the effectiveness of the bioreactor design of the present invention in establishing uniform flow circulation within each quadrant chamber, flow visualization studies were performed using a dye dispersion method. In order to visualize the flow, a transparent acrylic chamber was first prototyped in replacement of the polycarbonate translucent chamber of the bioreactor. Then the modified bioreactor was assembled with eight cartridges suspended within the chamber and connected to a water flow circuit. Next, commercially available dye was injected through the inlet, and a sequence of snapshots were taken at 1 minute intervals to document the dye distribution into the quadrant chamber of the bioreactor.

Changes in urea concentration were quantitatively measured using a urea nitrogen (BUN) kit, based on direct interaction of urea with diacetyl monoxime. The absorbance was measured at 540 nm with a multi-detection microplate reader. Culture medium containing 5.0 mM ammonia chloride was added to the cells in order to evaluate the ammonia clearance ability of the hepatocytes. Furthermore, albumin secretion was measured by a standard competitive enzyme linked immunosorbent assay (ELISA) with the use of purified rat albumin and peroxidase conjugated sheep anti-rat albumin antibody. Briefly, 50 J, g/ml rat albumin was added to 96 well plates and stored at 4° C. for at least 24 hours. The wells were washed with 0.05% Tween-20 in PBS and non-specific binding sites were blocked with Tween-20 at the same time. 50 µl of sheep anti-rat albumin peroxidase conjugate were added to each well and incubated for 24 hours at 4° C. The wells were then washed with 0.05% Tween-20 four times and incubated for 15 minutes with o-phenylenediamine substrate. The reaction was stopped with 8 N sulfuric acid and absorbance was measured at 450 nm with the multi-detection microplate reader. Both the urea and albumin results were calibrated to a standards curve, and concentration values were normalized by the nutrient medium volume, culture time, and number of seeded hepatocytes.

An important function of hepatocytes is to metabolize thousands of endogenous and exogenous compounds by a large group of heme-containing isoenzymes, i.e. cytochrome P450 (CYP). They primarily locate in hepatocytes, within the membranes of the smooth endoplasmic reticulum. For rat primary hepatocytes, CYP1 enzymes are present at a relatively higher level and are readily detectable as compared to other CYP families. Ethoxyresorufin-O-deethylase (EROD) activity has been used as a catalytic monitor of CYP1 enzymes (primarily CYP1A1). Using ethoxyresorufin as the substrate, the rate of resorufin productivity is directly proportional to the EROD activity.

Sandwich cultures in 24-well plastic culture plates were used as negative and positive controls. CYP1A1/2 was induced by adding 2 µM 3-methylcholanthrene (3MC) to the medium for 48 hours before the EROD assay. Three samples were used to perform each EROD assay. Each cartridge or the culture plate well was incubated in a Hank's Balanced Salt Solution (HBSS) buffer containing 20 mM HEPES and 10 µM dicumarol, which inhibits the secondary metabolism of resorufin. After 10 minutes of incubation, assay buffer containing 5 µM ethoxyresorufin and 10 µM dicumarol was added. After 1 hour of incubation in 5% $CO_2$, 95% air at 37° C., the assay buffer was sampled at various time points (5, 15, 25, and 35 min). The cells in the cartridges and in the 24-well culture plates were washed twice with HBSS, fed with fresh medium and returned to either the bioreactor or the incubator. Resorufin fluorescence (with excitation at 530 nm, and emission at 590 nm) was measured using the multi-detection microplate reader. To determine the net resorufin production, a resorufin standard curve (range 2 to 200 pmol) was used. Before serial dilution, the actual concentration of the super stock of resorufin, 200 µM in HEPES (pH9), was checked on each assay date using a spectrophotometer. The actual concentration was calculated using the Beer-Lambert Law, $C=A/sL$. Where C is the concentration, A is the wavelength, s is the molar absorption coefficient, and L is the width of sample cuvettes (L=1 cm). Three replicates of each resorufin standard were added to a 96-well plate and the average background corrected arbitrary fluorescence units were plotted against the nominal resorufin concentrations to produce the resorufin standard curve and linear regression equation. The resorufin content in each well was plotted against time and a linear regression analysis was performed on each sample well to obtain the slope and estimate the resorufin production rate (pmol/min). The results were normalized by the dilution of medium and number of seeded hepatocytes.

To evaluate the $O_2$ environment established within bioreactor assembly, a single quadrant chamber of the bioreactor assembly supporting eight cartridges was used. Tissue culture medium containing 0.2 mM Hypoxyprobe™-1 (Pimonidazole Hydrochloride, Chemicon, Temecula, Calif.) was circulated through the chamber for 4 hours. Meanwhile, three cartridges maintained at an incubator (5% $CO_2$, 21% C>2, 37° C.), were used as negative controls, whereas, another three cartridges maintained at the other incubator (5% $CO_2$, 1% C>2, 37° C.) were used as positive controls. Following the 4 hours incubation, samples were fixed in 4% paraformaldeyde (in 1×PBS) for 10 min at 4° C. and stored in PBS until staining. The following immunohistochemical staining protocol was employed, where all steps took place at room temperature and 1×PBS was used for washes. Endogenous peroxidase was blocked with 3% hydrogen peroxide in PBS for 10 minutes. Dako protein block, used to block potential non-specific binding sites in the cell/tissue, was applied for 15 minutes. Samples were then incubated with hypoxyprobe-1 Mab1 conjugated with FITC (clone 3.11.3) at 1:50 for 40 minutes. As the negative controls, no primary antibody was added to the cells. A rocking platform was used with a speed of 30 rpm and 10° tilt angle, to ensure that all the hepatocytes were stained evenly. Anti-FITC Mab conjugated with HRP was used as the secondary antibody at 1:300 for 30 min. Labeling was visualized using liquid diaminobenzidine (DAB) for 5 minutes. Samples were then counterstained with Mayer's haematoxylin and kept in 1×PBS for image analysis on the same day.

Cell viability was evaluated for hepatocytes within the static and dynamic systems, as compared with the control sandwich cultures on Day 2, Day 7, and Day 11. In each case, an inverted microscope was used to observe hepatocyte morphologies immediately prior to initiating the viability assay. To evaluate the viability of the hepatocytes cultured within the cartridges of the bioreactor assembly, the following procedure was followed. The media was first removed, then a small scissors was used to cut off the membranes from the cartridge. The modified sandwich cultures were then carefully relocated from the cartridges to labeled 60 mm tissue culture plates and incubated for 30 minutes with 1 ml of a viability solution consisting of 2 µM Calcein AM, 4 µM Ethidium Homodimer in media. A rocking platform was used with a speed of 30 rpm and 10° tilt angle to ensure that all the hepatocytes were stained evenly. Next, the cells were fixed with by 10% buffered formalin solution in PBS. Viable and non-viable cells were examined through the confocal microscopy using FITC and Texas red filter sets, respectively. Flouview v 2.1.39 and Metamorph Imaging system were then used to obtain and analyze the fluorescent images.

Each individual cartridge was first evaluated for the design's effectiveness in supporting hepatocyte viability, differentiation, and liver specific functions. This helped verify whether the cartridge configuration provided a favorable environment for the hepatocytes. Culturing hepatocytes in a traditional sandwich configuration between two layers of gelled extracellular matrix prolongs the time of cultures by displaying polygonal morphology, maintaining cell viability and hepatocyte specific functions up to several weeks. The traditional collagen sandwich culture within 35 mm tissue culture plates was used as the control. The cartridge configuration was tested under both static condition and dynamic condition. Since cell-cell interactions strongly influence hepatocyte function in collagen gel, seeding density was consistently kept as $2.1 \times 10^5$ cells/cm$^2$ in both the controls and cartridges to ensure comparable results.

First, morphologies of hepatocytes cultured in different conditions were observed daily. Within the cartridge, hepatocytes were sandwiched between a collagen type I dried film treated cartridge membrane and collagen gel, as compared to the traditional sandwich culture configuration. During the first one hour of seeding, hepatocytes attached and started to spread on both the dried collagen film coated cartridge membrane and the collagen gel surface. However, the collagen film coated cartridge membrane resulted in the cells spreading quickly and a better interconnect between neighboring cells within the 24 hours before the second layer of collagen was overlayed during the culture. Similar to the control sandwich cultures, hepatocytes cultured within the cartridges developed and sustained polygonal morphology and exhibited distinct cell-cell borders for more than 11 days both in the static and dynamic systems.

Next, cell viabilities were evaluated for hepatocytes cultured in the above three conditions on day 2, day 7 and day 11 post-isolation. Cell viability in the cartridges (both in static and dynamic) remained relatively stable during the two week culture period. No significant difference was observed between hepatocyte viability for the controls and cartridge.

The effectiveness of individual cartridges in supporting hepatocytes was evaluated by comparing the liver specific functions, albumin and urea secretion. Albumin production and urea secretion were measured for both the static and dynamic systems, as compared with the control sandwich culture, throughout the 15 day culture period.

Albumin is a highly soluble, single polypeptide protein with a molecular weight of 66,000. It has been often measured as an indication of synthetic activity of hepatocytes. Although hepatocytes have 12% higher albumin production rates when cultivated in the static cartridge system (peaking at $67.54 \pm 23.56$ μg/$10^6$ cells/day, n=3) than the control ($60.24 \pm 21.68$ μg/$10^6$ cells/day, n=3), this difference was not statistically significant. Contrastingly, in the dynamic system, hepatocytes significantly increase the albumin secretion rate after Day 5 compared with either the static system or the control (p<0.025). The peak albumin secretion rate for the dynamic system reached an average value of $170.03 \pm 22.02$ μg/$10^6$ cells/day (n=3).

Urea secretion is an indicator of metabolic function of hepatocytes. To evaluate the urea secretion rate of hepatocytes cultured in three conditions, all cultures were spiked with ammonia on Day 7. The urea secretion rate of hepatocytes cultured in the control sandwich culture configuration was highest in the first 3 to 5 days post-isolation and averaged $97.32 \pm 6.93$ μg/$10^6$ cells/day (n=3). Secretion rate then further decreased after spiking by ammonia during the subsequent 1 week in culture. For the static culture system of the cartridge, urea secretion rate was stable and higher than the control over the 2 weeks of culture. Adding NH$_4$Cl did not cause a big fluctuation in urea the secretion rate of the static system. However, the pattern of urea secretion rate of the dynamic system was significantly different from that of either the control or static system. The peak of the secretion rate was on Day 5 post-isolation and decreased by roughly 40%. After spiked by adding ammonia, the secretion rate firstly increased and then decreased to a stable level during the last 4 days in culture. By circulating medium within the culture system, i.e. the dynamic system, the urea secretion rate was significantly improved compared with either the control or the static system.

These results confirmed the efficacy of the individual cartridge in supporting hepatocytes to maintain its morphological development and cell survival. Furthermore, the dynamic flow of nutrient media enhances the cellular functional performance. Next, the performance of the bioreactor assembly with a perfusion system was evaluated. As shown from a series of snapshots of dye dispersion within a bioreactor chamber, the dye was initially injected from the bottom outlet. It quickly filled the chamber bottom up. To leave the bioreactor, dye solution was drawn by a peristaltic pump (Q=60 ml/min) through a central tube, which was used as an outlet. The unique flow pattern was therefore created.

Next, the evaluation of the bioreactor assembly in supporting hepatocytes was performed. Since the pH and O$_2$ levels are critical to cell survival and functional performance, medium was sampled to monitor these two parameters throughout the two week culture period of each experiment. The pH of the tissue culture medium ranged from 6.9 to 7.5. The ideal physiological range is 7.2 to 7.4, but it did not have a detrimental effect on cell viability.

O$_2$ diffusion could be facilitated by increasing the pC>2 by using 95% O$_2$ plus 5% CO$_2$. Nevertheless, to avoid hyperoxia encountered by hepatocytes, 21% O$_2$/5% CO$_2$ and balanced with N$_2$ was used during the oxygenation of nutrient media. The other way to augment the oxygen transfer rate is to increase the flow rate of the system. Because the unique membrane-frame design protected the encased cellular spaces from shear stress of flow, the flow rate was set at a relatively high value, i.e. 60 ml/min, without disturbing the cells. The dissolved O$_2$ in the medium was measured at both inlet and outlet of the bioreactor assembly, ranging from 6.6 mg/L to 8.2 mg/L.

To ensure that the nutritional demands of the contained hepatocytes were met, the oxygen uptake rate (OUR) was also examined. The OUR was calculated as below, $$OUR = \frac{(DO_{inlet} - DO_{outlet}) * Q}{N}$$

where DO is the dissolved oxygen concentration (mg/L) in the inlet and outlet of bioreactor assembly, Q is the culture medium flow rate (ml/min), and N is the number of cells in the bioreactor.

Hypoxyprobe™ was used as an alternative approach to test the suitability of oxygen level within the bioreactor. Regions of hypoxia were assessed on Day 2 post-isolation, which is the first day of culture in the cartridge within the bioreactor assembly. After 4 hours of perfusion, hepatocytes located at the bottom region of the bioreactor (close to the inlet) were compared with the cells in the upper region (close to the outlet). As a positive control, hepatocytes were stained with hypoxyprobe-1 after incubation in hypoxic conditions (1% O$_2$) for 4 hours. Contrastingly, for the negative control, hepatocytes were incubated in normoxic conditions (21% O$_2$), which were stained only by the hematoxylin. In comparison to the positive and negative controls, there was no indication of severe hypoxia in the hepatocytes located at either the bottom or the top of the bioreactor assembly. This result suggests that the unique flow pattern of the bioreactor assembly provides a normoxic environment for the cells in the cartridge.

Evaluation of the success of the bioreactor assembly in supporting the viability and functional performance of its cultured hepatocytes was then performed. During the 15 day culture period, hepatocyte morphologies were documented at various times. Hepatocytes within the perfused bioreactor maintained morphologies similar to that observed for hepatocytes in the individual cartridge in the dynamic culture system. At the end of the 15 day perfusion, cartridges were removed from the bioreactor, and hepatocyte viability was evaluated. The average viability was 84±18% (n=3).

The albumin production and urea secretion rates achieved by the hepatocytes maintained in the bioreactor were obtained. The secretion rates, normalized by the dilution of the culture medium and number of cells, were comparable to the previous results achieved for hepatocytes in individual cartridges. The culture of hepatocytes within the bioreactor assembly started on Day 2 post-isolation. On Day 6 and Day 12, the media of the chamber and flow circuit were replaced with fresh media containing 5 mM ammonia chloride ($NH_4Cl$), which was used to spike hepatocytes cultured with the bioreactor assembly, to evaluate their success in ammonia clearance. The rate of albumin secretion rapidly increased to 126.64±9.54 µg/$10^5$ cells/day and 110.20±15.61 µg/$10^6$ cells/day on day 11 and day 15, respectively. The time course of urea secretion during the two weeks of bioreactor perfusion was also obtained. After addition of $NH_4Cl$ to the tissue culture medium on day 6 and day 12, a progressive increase in urea synthesis was detected.

The inducibility of EROD was studied by adding 3-MC. Induction was initiated on day 6 and day 12 and was continued for 3 days. EROD activity on day 9 and day 15 were evaluated. The hepatocytes cultured in 24-well culture plates were used as the control for comparison. The resorufin production rates were normalized by the dilution of the incubation buffer and number of cells. On day 3, before adding inducer, the cells both in the plates and bioreactor have very low EROD activity. After the addition of 3-MC, a maximum induction of EROD activity was obtained in both systems and peaked on day 9. The addition of inducer 3-MC had 48.5% and 56.6% higher effect on the enzyme activity in cells from the bioreactor than the controls on day 9 and day 15, respectively.

For a bioreactor design to be successful, it is critical that it establishes a uniform environment for the cells it contains, and supports live and functioning cells. Various radial flow bioreactor designs have been used by several groups attempting to overcome this challenge (Iwahori et al. 2005; Miskon et al. 2007; Morsiani et al. 2001). From their results, radial flow design shows its advantages. Recent advances in the development of hepatocyte culture techniques, such as ECM enhancement techniques, micropatterning techniques, cell spray techniques, etc., provide possibilities to enhance hepatocellular functional performance by co-culturing the parenchyma and non-parenchyma cells. This symmetrically radial flow bioreactor was designed with great flexibility. The results of dye dispersion tests confirm that uniform flow is established within the bioreactor. On the other hand, by using Hypoxyprobe, no severe hypoxia was detected in the hepatocytes within the bioreactor. In evaluating hepatocyte performance within the cartridges of the bioreactor, the cells were found to maintain cell patterns similar to that of the sandwich cultures traditionally used to mimic cells in vivo. The cells in the cartridge were also able to achieve higher performance (i.e. ammonia clearance and albumin secretion) output for 2 weeks or more—again compared to the sandwich cultures as controls. Evaluations of the hepatocytes' ability to produce liver specific enzymes when housed within the bioreactor also indicate favorable results, the inducibility of EROD activity in hepatocytes maintained within the bioreactor is 30% higher than the sandwich culture in the plastic culture plates. These results demonstrate that hepatocytes perform well within the bioreactor. This is consistent with design expectations, since its cartridge design and dynamic flow enable the cells to access nutrients from two sides of the monolayer of cells. The nutrient transport barrier to the cells has been minimized to be less than 80 µm (including 30 µm of membrane thickness). This feature of enabling multi-directional mass transport is also achieved in the natural organ, in vivo. Furthermore the bioreactor establishes a uniform microenvironment for the cells it supports. This is important since the cells of the current study were isolated from an animal source (rather than a genetically engineered cell line). As such, the favorable microenvironment encourages the cells to quickly adjust to, and perform within, this novel in vitro system. As such, the results indicate that the novel bioreactor with a symmetric design is a successful system for maintaining large numbers of live and functioning cells for use in biomedical applications.

Again, it should be noted that, although the bioreactor assembly of the present invention is described herein largely in terms of liver support applications, its broader applicability is not so limited, as those of ordinary skill in the field will readily understand and appreciate. Many applications that are currently known and that have yet to be developed are contemplated by the present invention. At present, bioreactors are used in bioartificial organs, organ and tissue simulation, drug discovery and testing, cell/tissue manufacturing, antibody production, and, in general, the study and use of biochemical reactions (including those involving organisms, substances derived from or affecting organisms, cellular structures, etc.), as examples. Quite simply, the bioreactor assembly of the present invention may be used in any application that a bioreactor of any type is suitable for.

Although the present invention has been illustrated and described herein with reference to preferred embodiments and specific examples thereof, it will be readily apparent to those of ordinary skill in the field that other embodiments and examples may perform similar functions and/or achieve like results. All such equivalent embodiments and examples are within the spirit and scope of the present invention, are contemplated thereby, and are intended to be covered by the following claims.

What is claimed is:

1. A bioreactor assembly, comprising:
    a housing internally defining a plurality of reaction chambers;
    a medium flow supply line associated with each of the plurality of reaction chambers, wherein the medium flow supply line associated with each of the plurality of reaction chambers is operable for delivering a medium flow to each of the plurality of reaction chambers;
    one or more framed membrane cartridges selectively disposed within each of the plurality of reaction chambers, wherein each of the one or more framed membrane cartridges disposed within each of the plurality of reaction chambers is operable for holding a biochemically active material that is reacted when exposed to the medium flow; and
    a rack that engages a top portion of the housing and to which the one or more framed membrane cartridges are selectively attached, wherein each of the one or more framed membrane cartridges are hung from the rack within the housing in a substantially vertical configuration, and wherein each of the one or more framed membrane cartridges are hung from the rack within the housing independent from other framed membrane cartridges;

wherein each of the one or more framed membrane cartridges comprises one or more thin film membrane substrates, an attachment layer for attaching the biochemically active material to the one or more thin film membrane substrates, and a protective layer for protecting the biochemically active material from the medium flow that are attached to a rigid frame around a periphery thereof and span an opening defined by the rigid frame.

2. The bioreactor assembly of claim 1, wherein the housing comprises a perimeter wall, a bottom wall, and one or more internal walls that collectively define the plurality of reaction chambers.

3. The bioreactor assembly of claim 2, wherein the one or more internal walls prevent fluid communication among the plurality of reaction chambers.

4. The bioreactor assembly of claim 1, wherein the medium flow delivered to each of the plurality of reaction chambers is a common medium flow.

5. The bioreactor assembly of claim 1, wherein the one or more framed membrane cartridges disposed within each of the plurality of reaction chambers are disposed substantially concentrically about a central axis of the housing.

6. The bioreactor assembly of claim 1, wherein the biochemically active material is selectively disposed one of on and between the one or more membrane substrates.

7. The bioreactor assembly of claim 6, wherein one or more of the one or more membrane substrates are substantially porous, such that fluid transport may take place there through.

8. The bioreactor assembly of claim 1, further comprising a cover operable for selectively engaging and environmentally sealing the housing.

9. The bioreactor assembly of claim 1, wherein the medium flow within each of the plurality of reaction chambers is one or more of radial and vertical.

10. A bioreactor method, comprising:
providing a housing internally defining a plurality of reaction chambers;
associating a medium flow supply line with each of the plurality of reaction chambers, wherein the medium flow supply line associated with each of the plurality of reaction chambers is operable for delivering a medium flow to each of the plurality of reaction chambers;
selectively disposing one or more framed membrane cartridges within each of the plurality of reaction chambers, wherein each of the one or more framed membrane cartridges disposed within each of the plurality of reaction chambers is operable for holding a biochemically active material that is reacted when exposed to the medium flow; and
providing a rack that engages a top portion of the housing and to which the one or more framed membrane cartridges are selectively attached, wherein each of the one or more framed membrane cartridges are hung from the rack within the housing in a substantially vertical configuration, and wherein each of the one or more framed membrane cartridges are hung from the rack within the housing independent from other framed membrane cartridges;
wherein each of the one or more framed membrane cartridges comprises one or more thin film membrane substrates, an attachment layer for attaching the biochemically active material to the one or more thin film membrane substrates, and a protective layer for protecting the biochemically active material from the medium flow that are attached to a rigid frame around a periphery thereof and span an opening defined by the rigid frame.

11. The bioreactor method of claim 10, wherein the housing comprises a perimeter wall, a bottom wall, and one or more internal walls that collectively define the plurality of reaction chambers.

12. The bioreactor method of claim 11, wherein the one or more internal walls prevent fluid communication among the plurality of reaction chambers.

13. The bioreactor method of claim 10, wherein the medium flow delivered to each of the plurality of reaction chambers is a common medium flow.

14. The bioreactor method of claim 10, wherein the one or more framed membrane cartridges disposed within each of the plurality of reaction chambers are disposed substantially concentrically about a central axis of the housing.

15. The bioreactor method of claim 10, wherein the biochemically active material is selectively disposed one of on and between the one or more membrane substrates.

16. The bioreactor method of claim 15, wherein one or more of the one or more membrane substrates are substantially porous, such that fluid transport may take place there through.

17. The bioreactor method of claim 10, further comprising providing a cover operable for selectively engaging and environmentally sealing the housing.

18. A bioreactor assembly, comprising:
a housing internally defining a plurality of reaction chambers;
a medium flow supply line associated with each of the plurality of reaction chambers, wherein the medium flow supply line associated with each of the plurality of reaction chambers is operable for delivering a medium flow to each of the plurality of reaction chambers; and
one or more framed membrane cartridges selectively disposed within each of the plurality of reaction chambers, wherein each of the one or more framed membrane cartridges disposed within each of the plurality of reaction chambers is operable for holding a biochemically active material that is reacted when exposed to the medium flow, and wherein one or more of the one or more framed membrane cartridges disposed within a given reaction chamber may be selectively removed without disrupting reactions taking place in other reaction chambers; and
a rack that engages a top portion of the housing and to which the one or more framed membrane cartridges are selectively attached, wherein each of the one or more framed membrane cartridges are hung from the rack within the housing in a substantially vertical configuration, and wherein each of the one or more framed membrane cartridges are hung from the rack within the housing independent from other framed membrane cartridges;
wherein each of the one or more framed membrane cartridges comprises one or more thin film membrane substrates, an attachment layer for attaching the biochemically active material to the one or more thin film membrane substrates, and a protective layer for protecting the biochemically active material from the medium flow that are attached to a rigid frame around a periphery thereof and span an opening defined by the rigid frame.

19. The bioreactor assembly of claim 18, wherein the bioreactor assembly is maintained at predetermined environmental conditions.

20. The bioreactor assembly of claim 18, wherein the bioreactor assembly is used in an application selected from the group consisting of a bioartificial organ application, an organ modeling application, an organ simulation application, a drug discovery application, a drug testing application, a cell/tissue manufacturing application, an antibody production application, and another biochemical reaction application.

\* \* \* \* \*